United States Patent [19]
Dornoff et al.

[11] Patent Number: 5,916,576
[45] Date of Patent: Jun. 29, 1999

[54] METHOD OF SCAVENGING FREE RADICALS USING ORANGE EXTRACT

[75] Inventors: Jeffrey M. Dornoff, Grand Rapids, Mich.; Michael B. Davies, Chattanooga, Tenn.

[73] Assignee: Amway Corporation, Mich.

[21] Appl. No.: 08/865,913

[22] Filed: May 30, 1997

[51] Int. Cl.⁶ ........................................ A61K 7/00
[52] U.S. Cl. ...................... 424/401; 424/195.1; 424/400; 514/873; 514/937; 514/945; 514/970
[58] Field of Search ................................ 424/195.1, 401, 424/400; 514/970

[56] References Cited

U.S. PATENT DOCUMENTS

| | | |
|---|---|---|
| 1,990,676 | 2/1935 | Stern . |
| 2,255,341 | 9/1941 | Wilson . |
| 4,460,488 | 7/1984 | Grollier et al. . |
| 5,073,545 | 12/1991 | Arima et al. . |
| 5,152,990 | 10/1992 | Miyauchi . |
| 5,167,954 | 12/1992 | Frey . |
| 5,362,494 | 11/1994 | Zysman et al. . |
| 5,445,747 | 8/1995 | Kvietok et al. ............................ 252/86 |
| 5,482,710 | 1/1996 | Slavtcheff et al. . |
| 5,560,907 | 10/1996 | Sakai et al. . |
| 5,702,691 | 12/1997 | Ichinose et al. ....................... 424/70.1 |
| 5,780,086 | 7/1998 | Kirksey et al. .......................... 426/546 |

FOREIGN PATENT DOCUMENTS

| | | |
|---|---|---|
| 7-17846 | 1/1995 | Japan . |
| 7-25762 | 1/1995 | Japan . |
| 7-97311 | 4/1995 | Japan . |

*Primary Examiner*—Thurman K. Page
*Assistant Examiner*—James M. Spear
*Attorney, Agent, or Firm*—G. Peter Nichols; Brinks Hofer Gilson & Lione

[57] ABSTRACT

The present invention relates to the use of orange extract for the preparation of pharmaceutical, cosmetic, food or agricultural compositions with an anti-radical activity. The orange extract is substantially free from ascorbic acid.

18 Claims, No Drawings

METHOD OF SCAVENGING FREE RADICALS USING ORANGE EXTRACT

BACKGROUND OF THE INVENTION

The present invention relates to a method of scavenging free radicals by incorporating orange extract into a composition.

The deleterious effects of free radicals are, in many cases, known but are continually being investigated. For example, it is believed that one of the causes of the deterioration of skin over time is the formation of free radicals within the elements forming the skin such as the fibers, cells and enzymes. The formation of free radicals may be caused, in part, by the action of external radiation of sunlight. The free radicals thus formed may attack the skin elements through a chain reaction that continues as long as the free radical exists, i.e., as long as the free radical does not combine with something (typically called a scavenger or inhibitor) that produces a stable molecule. The adverse action of these free radicals at the cutaneous integument level may cause destruction of cell DNA and an erosion of the connective tissues (collagen and elastin). Thus, the skin looks more aged.

As a result, substances that interrupt or inhibit the formation of free radicals during the free radical chain reaction are continually being sought. At the present, well known scavengers (also referred to as inhibitors or antioxidants, and as used in the following specification and appended claims should be considered synonymous with scavenger) include phenols, aromatic amines, sulfur compounds, raw seed oils, wheat germ oil, tocopherols, and gums. It is also believed that phosphoric acid, citric acid, and ascorbic acid have their own scavenging activity or enhance the activity of the known scavengers mentioned above.

Thus, French Demande 2,597,337-A2 describes a cosmetic to slow down the aging process by attacking free radicals. The cosmetic includes a first water soluble active ingredient, which may include a source of vitamin C such as from acerola cherry extract, and a second fat soluble ingredient, which includes free radical scavengers such as vitamin E.

While the above French Demande describes the use of acerola cherry extract, it is particularly with respect to the presence of vitamin C, known to be present in relatively high amounts when compared to other natural sources of vitamin C. Likewise, Japanese Laid-open applications 2-200610 and 70-61915 describe that an extract obtained from fruits of acerola may be incorporated into cosmetics. Those applications teach that the acerola cherry contain vitamin C or ascorbic acid and application no. 2-200610 describes the extract as containing at least 1% L-ascorbic acid and it is the presence of the L-ascorbic acid that provides the desired whitening effect. This is not surprising since, it is well known that L-ascorbic acid provides a whitening effect.

There is, however, no appreciation that an orange extract, which is substantially free of vitamin C, has free radical scavenging activity. The present inventors have now found that an orange extract exhibits free radical scavenging activity and, as a result may find particular application in the preparation of pharmaceutical, food and agricultural compositions, and more particularly in cosmetics for external skin application. Thus, the ability of the orange extract used in the present invention to scavenge free radicals is surprising and unexpected.

SUMMARY OF THE INVENTION

It is an object of the present invention to provide compositions that inhibit the formation of or scavenge the presence of free radicals. The present invention also contemplates that compositions containing known free radical scavengers can be enhanced by incorporating orange extract. Thus, the present invention includes a composition of the type containing free radical scavengers wherein the improvement comprises adding orange extract. Preferably, the composition is a cosmetic composition suitable for use on human skin. For example, the orange extract may have application alone or in conjunction with skin whitening agents for use as a skin whitener.

The present invention also includes a method of providing free radical scavenging activity in a composition comprising admixing to the composition an effective amount of orange extract to increase the free radical scavenging activity of the composition.

It is known that the superoxide ions produced during oxidation reactions caused by molecular oxygen are very active and in particular attack proteins and nucleic acids. Thus, the present invention is based on the anti-radical activity of orange extract towards the superoxide radical. The compositions of the present invention incorporating the orange extract are particularly suitable for protecting the skin due in particular to the protection against phototoxic reactions and UV aggression.

The present invention also includes a method of scavenging free radicals in human skin comprising topically applying to the skin a composition comprising orange extract. Preferably, the composition further includes a pharmaceutically acceptable carrier.

The orange extract useful in the present invention is substantially free from ascorbic acid and contains only minor amounts of organic acids particularly carboxylic acids.

The term "substantially free from ascorbic acid" as used in the specification and accompanying claims means that any ascorbic acid present in the orange extract is present in an amount no greater than about 1% by weight, preferably no greater than about 0.1%, and more preferably no greater than about 0.01% of the orange extract. Most preferably, the ascorbic acid, if present, is present in an amount no greater than about 0.005% of the orange extract.

The term "minor amounts of organic acids" and "minor amounts of carboxylic acids" as used in the specification and accompanying claims means that any organic acid and any carboxylic acid, which includes saturated and unsaturated carboxylic and dicarboxylic acids, hydroxymonocarboxylic acids, hydroxydicarboxylic acids, and hydroxytricarboxylic acids, is present in an amount no greater than about 5% by weight, preferably no greater than about 3%, and more preferably no greater than about 2% of the orange extract.

In the composition according to the present invention, the amount of orange extract to be used can not be absolutely specified because it varies according to the form of preparation. However, it is generally used in an amount from about 0.01% to about 50%, preferably from about 0.01% to about 5%, desirably from about 0.05% to about 2%, more preferably from about 0.1% to about 1% based on the whole weight of the composition.

It is noted that, unless otherwise stated, all percentages given in this specification and the appended claims refer to percentages by weight.

DETAILED DESCRIPTION OF THE INVENTION

In accordance with the present invention, a free radical scavenger composition is provided which comprises orange extract as an active ingredient.

In the present invention, however, the orange extract is substantially free from any substantial amount of vitamin C (ascorbic acid or its derivatives). In other words, the orange extract does not contain more than about 1% by weight, preferably no greater than about 0.1%, and more preferably no greater than about 0.01% of the orange extract. Most preferably, the ascorbic acid, if present, is present in an amount no greater than about 0.005% of the orange extract.

The orange extract can be made in any suitable manner to achieve an extract that is substantially free of ascorbic acid. Preferably, the orange extract is obtained from orange peel, flowers, and/or leaves on an orange tree. It is believed that the orange extract is prepared by drying the material, pretreating it, cold extracting the the pretreated material by alternating maceration and percolation for 24 to 48 hours, filtrating, microfiltrating, and adding a suitable preservtive such as parabens or phenoxyethanol. Most preferably, the orange extract is Bitter Orange Peel Extract HB from Centerchem, Inc. or Herbasol Orange Extract from Cosmetochem. It is believed that the Centerchem material is obtained from the orange peel while the Cosmetochem material is obtained from the orange flower.

In the composition according to the present invention, the amount of orange extract to be used can not be absolutely specified because it varies according to the form of preparation. However, it is generally used in an amount from about 0.01% to about 50%, preferably from about 0.01% to about 5%, desirably from about 0.05% to about 2%, more preferably from about 0.1% to about 1% based on the whole weight of the whitener composition.

The composition of the present invention may be prepared in various forms. For example, it may be in the form of a cosmetic preparation such as cream, cosmetic lotion, pack or powder, or as an emulsion, lotion, liniment or ointment. In each formulation, various known conventional cosmetic ingredients may be incorporated. For example, cosmetic ingredients such as alcohols, fats and oils, surfactants, fatty acids, silicone oils, humectants, viscosity modifiers, emulsifiers, stabilizers, coloring agents, and perfumes.

In another aspect of the composition of the present invention there is provided an improved free radical scavenging composition wherein the improvement comprises adding orange extract, as fully defined above. In this aspect, it may be desirable to incorporate the orange extract in, for example, a skin whitening composition. In this instance, the free radical scavenging activity of the orange extract can inhibit the conversion of dopaquinone with the result of inhibiting the production of eumelanin. Consequently, it is contemplated that the free radical scavenging activity of the orange extract can augment the known tyrosinase inhibitors and thus, provide enhanced skin whitening properties.

The present invention also contemplates a method of enhancing the free radical scavenging activity of known free radical scavengers that comprises adding orange extract to compositions containing known free radical scavengers.

The present invention also includes a method of providing free radical scavenging activity in a composition comprising admixing to the composition an effective amount of orange extract to increase the free radical scavenging activity of the composition.

In another aspect of the present invention, a method of scavenging free radicals in human skin is provided and comprises topically applying to the skin orange extract. More preferably, the method comprises topically applying to the skin a composition comprising orange extract and a pharmaceutically acceptable carrier. The term "pharmaceutically acceptable" means those drugs, medicaments, or inert ingredients which are suitable for use in contact with the tissues of humans and lower animals without undue toxicity, incompatibility, instability, irritation, and the like, commensurate with a reasonable benefit/risk ratio.

To demonstrate the free radical scavenging activity of the orange extract of the present invention, the test described in Cosmetics & Toiletries, Vol. 10, pp. 51–56, October 1995) was conducted.

A control solution was prepared by measuring 39.43 mg of 2,2-diphenyl-1-picrylhydrazyl hydrate (DPPH), a known source of free radicals, and diluting it to 1000 ml with ethanol. A control cuvette was charged with 1.75 ml of the control and 1.75 ml of ethanol. A blank cuvette was charged with 3.5 ml of ethanol. The cuvettes were placed in an oven for 30 minutes at 37° C. The absorbency was measured at 516 nm using a UV/vis spectrophotometer by placing the blank cuvette into the reference slot and the control cuvette into the sample slot.

EXAMPLE 1

An orange extract was prepared according to the method described above. A test cuvette was charged with 1.75 ml of the control solution and 1.75 ml of a 1% solution of orange extract. A reference cuvette was charged with 1.75 ml of the orange extract and 1.75 ml of ethanol. The cuvettes were placed in an oven for 30 minutes at 37° C. The absorbency was measured in the manner described above with the test cuvette placed in the sample slot and the reference cuvette placed in the reference slot.

The free radical scavenging activity was calculated as a percentage of inhibition of the generation of the free radicals using the following formula:

$$\text{Percent Inhibition} = 100 \times [1 - (DT/DR)]$$

DT is the measured absorbance of the test cuvette with respect to the reference cuvette and DR is the measured absorbance of the control cuvette with respect to the blank cuvette.

The orange extract exhibited 52% inhibition.

This test shows that the orange extract has anti-radical activity and would therefore be expected to show beneficial results when incorporated into compositions.

EXAMPLE 2

Scavenging activity tests were conducted in the manner described in Example 1 using 1% solutions of (a) tocopheryl acetate, (b) rose hips oil, (c) tioxolone, and (d) Lanachrys 2B. The results are presented in Table 1 below.

TABLE 1

| WHITENER | % INHIBITION |
|---|---|
| Tocopheryl Acetate | 67 |
| Rose Hips Oil | 63 |
| Tioxolone | 50 |
| Lanachrys 2B | 40 |

It should be understood that a wide range of changes and modifications can be made to the embodiments described above. It is therefore intended that the foregoing description illustrates rather than limits this invention, and that it is the following claims, including all equivalents, which define this invention.

What is claimed:

1. A cosmetic composition comprising orange extract and a pharmaceutically acceptable carrier, wherein the orange extract is obtained from orange peel, orange flowers, or orange leaves and contains less than about 1% by weight ascorbic acid.

2. A method of providing anti-radical activity in a composition selected from the group consisting of pharmaceutical, cosmetic, food, and agricultural compositions, comprising admixing to the composition an effective amount of orange extract to increase the anti-radical activity of the composition, wherein the orange extract contains less than about 1% by weight ascorbic acid.

3. In a cosmetic composition in the form of a lotion, foam, creme, pack, powder, emulsion, liniment, or ointment, the improvement comprising an effective amount of orange extract to provide anti-radical activity towards a superoxide radical, wherein the orange extract is obtained from orange peel, orange flowers, or orange leaves and contains less than about 1% by weight ascorbic acid.

4. The method of claim 2, wherein the composition includes from about 0.01% to about 50%, by weight, orange extract.

5. A method of providing anti-radical activity in a cosmetic composition, comprising admixing to the composition an effective amount of orange extract to increase the anti-radical activity of the cosmetic composition, wherein the orange extract is obtained from orange peel, orange flowers, or orange leaves.

6. The method of claim 5 wherein the orange extract contains less than about 1% by weight ascorbic acid.

7. The method of claim 6, wherein the composition is selected from the group consisting of pharmaceutical, cosmetic, food, and agricultural compositions.

8. A method of scavenging free radicals in human skin comprising applying a composition comprising orange extract.

9. The method of claim 8 wherein the orange extract contains less than about 1% by weight ascorbic acid.

10. A skin whitening composition containing a skin whitener, the improvement comprising an effective amount of orange extract.

11. The composition of claim 10 wherein the orange extract contains less than about 1% by weight ascorbic acid.

12. The composition of claim 1 wherein the orange extract is present in an amount from about 0.01% to about 50%, by weight.

13. The composition of claim 1 wherein the orange extract is present in an amount from about 0.01% to about 5%, by weight.

14. The composition of claim 1 further comprising a skin whitener.

15. The method of claim 5, wherein the composition includes from about 0.01% to about 50%, by weight, orange extract.

16. The method of claim 8, wherein the composition includes from about 0.01% to about 50%, by weight, orange extract.

17. The method of claim 8, wherein the composition further includes a pharmaceutically acceptable carrier.

18. The method of claim 10, wherein the composition includes from about 0.01% to about 50%, by weight, orange extract.

* * * * *